(12) United States Patent
Kang et al.

(10) Patent No.: US 9,854,990 B2
(45) Date of Patent: Jan. 2, 2018

(54) BRAIN DISEASE DIAGNOSIS SERVICE APPARATUS AND BRAIN DISEASE DIAGNOSIS SERVICE METHOD

(71) Applicant: THE ASAN FOUNDATION, Seoul (KR)

(72) Inventors: Dong Wha Kang, Seoul (KR); Yong Hwan Kim, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 0 days.

(21) Appl. No.: 15/037,316

(22) PCT Filed: Nov. 18, 2014

(86) PCT No.: PCT/KR2014/011084
§ 371 (c)(1),
(2) Date: May 17, 2016

(87) PCT Pub. No.: WO2015/072818
PCT Pub. Date: May 21, 2015

(65) Prior Publication Data
US 2016/0302689 A1 Oct. 20, 2016

(30) Foreign Application Priority Data
Nov. 18, 2013 (KR) .................. 10-2013-0139853

(51) Int. Cl.
*G06K 9/00* (2006.01)
*A61B 5/055* (2006.01)
(Continued)

(52) U.S. Cl.
CPC ............ *A61B 5/055* (2013.01); *A61B 5/0037* (2013.01); *A61B 5/0042* (2013.01);
(Continued)

(58) Field of Classification Search
USPC .................................. 382/128–134
See application file for complete search history.

(56) References Cited

U.S. PATENT DOCUMENTS

| 2002/0026116 A1* | 2/2002 | Schmainda ............ A61B 5/055 |
| | | 600/419 |
| 2004/0127799 A1 | 7/2004 | Sorensen et al. |

(Continued)

FOREIGN PATENT DOCUMENTS

| JP | 07-311834 A | 11/1995 |
| JP | 2005-237441 A | 9/2005 |

(Continued)

OTHER PUBLICATIONS

Korean Office Action for corresponding Korean Patent Application No. 10-2013-0139853 dated Aug. 16, 2015, citing the above reference(s).

(Continued)

*Primary Examiner* — Alex Liew
(74) *Attorney, Agent, or Firm* — Hauptman Ham, LLP

(57) ABSTRACT

The present disclosure relates to a brain disease diagnosis service apparatus including at least: a receiving unit for receiving an image of a subject to be diagnosed; a preprocessing unit for estimating a transformation matrix in order to align a predetermined standard image with the image received by the receiving unit, and for applying the estimated transformation matrix to a predetermined standard brain region map, thereby generating an individual brain region map for the subject to be diagnosed; a feature point extracting unit for calculating a ratio occupied by brain lesions for each brain region in the individual brain region map, generated by the preprocessing unit, of the subject to be diagnosed, thereby extracting feature points; and a disability type determining unit for determining a disability (Continued)

type on the basis of the ratio of the brain lesions, calculated by the feature point extracting unit, for each brain region.

10 Claims, 8 Drawing Sheets

(51) Int. Cl.
*A61B 5/00* (2006.01)
*G06T 7/00* (2017.01)
*G01R 33/56* (2006.01)

(52) U.S. Cl.
CPC .......... *A61B 5/4064* (2013.01); *G06T 7/0014* (2013.01); *A61B 2576/026* (2013.01); *G01R 33/5608* (2013.01); *G06T 2207/10088* (2013.01); *G06T 2207/30016* (2013.01)

(56) References Cited

U.S. PATENT DOCUMENTS

| | | |
|---|---|---|
| 2008/0183069 A1 | 7/2008 | Fujimoto |
| 2009/0093706 A1* | 4/2009 | Zhang .................... A61B 5/055 600/410 |

FOREIGN PATENT DOCUMENTS

| | | |
|---|---|---|
| KR | 10-2012-0050379 A | 5/2012 |
| KR | 10-2013-0082849 A | 7/2013 |
| KR | 10-1301490 B1 | 8/2013 |

OTHER PUBLICATIONS

International Search Report dated Mar. 5, 2015 for PCT/KR2014/011084, citing the above reference(s).

* cited by examiner (a)   (b)   (c)

(a)  (b)  (c)

US 9,854,990 B2

BRAIN DISEASE DIAGNOSIS SERVICE APPARATUS AND BRAIN DISEASE DIAGNOSIS SERVICE METHOD

CROSS-REFERENCE TO RELATED APPLICATIONS

The present application is a continuation of International Patent Application No. PCT/KR2014/011084, filed Nov. 18, 2014, which is based upon and claims the benefit of priority to Korea Patent Application No. 10-2013-0139853, filed on Nov. 18, 2013. The disclosures of the above-listed applications are hereby incorporated by reference herein in their entirety.

TECHNICAL FIELD

The present disclosure relates generally to a brain disease diagnosis service apparatus and a brain disease diagnosis service method, and more particularly, to a brain disease diagnosis service apparatus and a brain disease diagnosis service method which are capable of determining a disability type of a diagnostic subject catching a brain disease by using images obtained from a magnetic resonance imaging (MRI) apparatus.

BACKGROUND ART

This section provides background information related to the present disclosure, which is not necessarily prior art.

As society progresses, neurodegenerative diseases, such as Alzheimer disease, are increased. In the case of neurodegenerative diseases, since the neurodegenerative diseases relate to a brain, there is a need to provide a method of diagnosing a neurodegenerative disease without any invasion.

However, in the case of diagnosing a brain disease without any invasion, the accuracy may deteriorate.

To solve the problem described above, there have been disclosed a brain disease analysis apparatus and a method thereof capable of analyzing a brain disease in Korean Unexamined Patent Publication No. 10-2012-0050379 assigned to Samsung Electronics Co., Ltd., etc.

According to the related art including Korean Unexamined Patent Publication No. 10-2012-0050379, a brain disease analysis apparatus may extract feature vectors from MRI and functional MRI collected from treatment and control groups, based on a vacuum or activity difference related to a brain region, and may use the feature vector to determine whether a diagnostic subject has a brain disease.

However, although the brain disease analysis apparatus according to the related art may exactly determine only whether a diagnostic subject has a brain disease, the disability type and in addition, the significance of a lesion observed from an MRI image have been mainly deduced in dependence on the personal experience of a doctor.

Thus, there is a need to provide an advanced apparatus and method which are relatively independent from deviation between individual doctors, quantitative, objective, and capable of determining whether disease exists and in addition, the disability type thereof, and predicting the prognosis.

DISCLOSURE

Technical Problem

The problems to be solved by the present disclosure will be described in the latter part of the best mode for carrying out the embodiments.

Technical Solution

This section provides a general summary of the disclosure and is not a comprehensive disclosure of its full scope or all of its features.

According to one aspect of the present disclosure, there is provided an apparatus for servicing a brain disease diagnosis based on an image obtained from a magnetic resonance imaging (MRI) apparatus. The apparatus includes a receiving unit configured to receive an image of a diagnostic subject obtained from the MRI apparatus, a preprocessing unit configured to estimate a transformation matrix for matching a preset standard image to the image received from the receiving unit and apply the transformation matrix to a preset standard brain region map such that an individual brain region map of the diagnostic subject is generated, a feature extracting unit configured to calculate an occupancy ratio of a brain lesion of each brain region in the individual brain region map of the diagnostic subject generated from the preprocessing unit to extract a feature, and a disability type determining unit configured to determine a disability type based on the occupancy ratio of the brain lesion of each brain region calculated by the feature extracting unit.

According to another aspect of the present disclosure, there is provided a method of servicing a brain disease diagnosis based on an image obtained from a magnetic resonance imaging (MRI) apparatus. The method includes receiving an image of a diagnostic subject obtained from the MRI apparatus, estimating a transformation matrix for matching a preset standard image to the received image and applying the transformation matrix to a preset standard brain region map such that an individual brain region map of the diagnostic subject is generated, calculating an occupancy ratio of a brain lesion of each brain region in the generated individual brain region map of the diagnostic subject to extract a feature by, and determining a disability type based on the occupancy ratio of the brain lesion of each brain region calculated.

Advantageous Effects

The advantageous effects of the present disclosure will be described in the latter part of the best mode for carrying out the embodiments.

BEST MODE

Mode for Invention

The present disclosure will now be described in detail with reference to the accompanying drawing(s).

Figure 1:
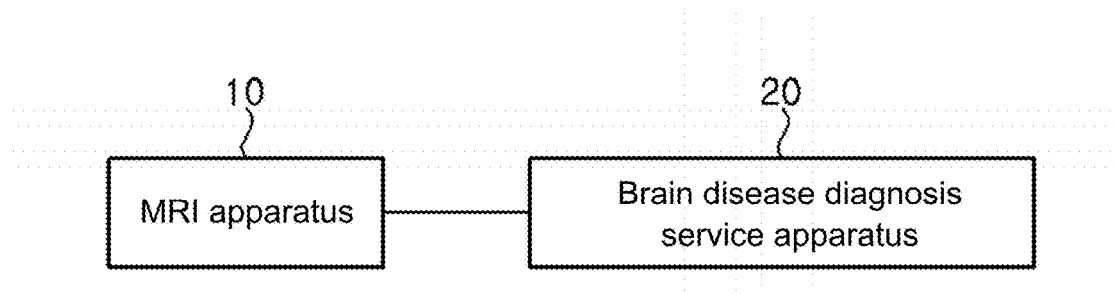
FIG. 1 is a block diagram illustrating a brain disease diagnosis service apparatus according to an embodiment of the disclosure.
Figure 2:
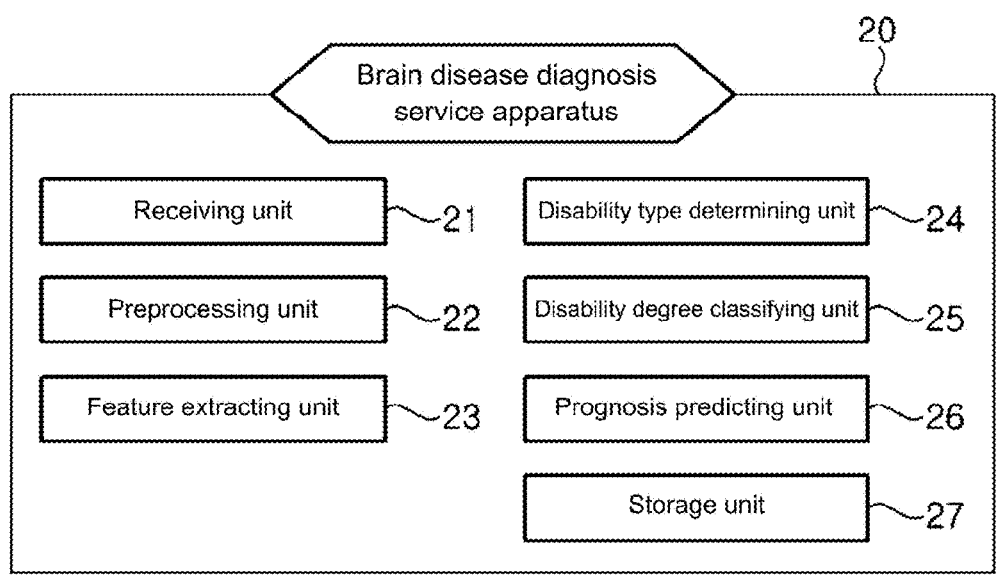
FIG. 2 is a block diagram illustrating in detail one example of the brain disease diagnosis service apparatus illustrated in FIG. 1.

FIG. 1 is a block diagram illustrating a brain disease diagnosis service apparatus according to an embodiment of the disclosure. FIG. 2 is a block diagram illustrating in detail one example of the brain disease diagnosis service apparatus illustrated in FIG. 1.

Referring to FIG. 1, a brain disease diagnosis service apparatus 20 according to an embodiment of the disclosure receives an image of a diagnostic subject obtained from an MRI apparatus 10 and preforms a preprocessing process for extracting brain lesion features from the received image to calculate a ratio of a brain lesion occupying a brain region of each extracted feature, such that the brain disease diagnosis service apparatus 20 determines a disability type.

In addition, the brain disease diagnosis service apparatus 20 may provide a prognosis of the disability type determined based on a degree of the occupancy ratio of a brain lesion. In this case, the prognosis is a result of comprehensively analyzing the prognoses of diagnostic subjects who are diagnosed with brain lesions of the same disability type and the occupancy ratios of the brain lesions of whom are within a predetermined reference range.

Referring to FIG. 2, the brain disease diagnosis service apparatus 20 includes a receiving unit 21, a preprocessing unit 22, a feature extracting unit 23, a disability type determining unit 24, a disability degree classifying unit 25, a prognosis predicting unit 26, and a storage unit 27.

The receiving unit 21 receives images of a diagnostic subject such as ADC, DWI and GRE images obtained from the MRI apparatus 10. In this case, the MRI apparatus 10 and the brain disease diagnosis service apparatus 20 may be connected to each other through a wire or wireless communication scheme.

The preprocessing unit 22 matches the ADC and DWI images received through the receiving unit 21 with each other. In this case, a region in which a brain lesion is placed is represented as a dark color (for example, black) in the ADC image. To the contrary, a region in which a brain lesion is placed is represented as a bright color (for example, white) in the DWI image. The preprocessing unit 22 may exactly extract a position of a brain lesion by matching the ADC and DWI image with each other.

In addition, the preprocessing unit 22 may estimate an affine transformation matrix to match a standard image previously known (a standard T2 enhancement image is used in the embodiment) with the GRE image received through the receiving unit 21 and may generate a standard T2 image transferred into a brain form of a diagnostic subject through the estimated affine transformation matrix.

For example, a published standard image, which is included in an SPM (Statistical Parametric Mapping) tool box provided by Wellcome Trust Centre for Neuroimaging of UCLA (University of California at Los Angeles), may be used as the standard T2 enhancement image (hereinafter, referred to as a 'standard T2 image'). The standardization was performed by matching coordinating the T2 enhancement images of 152 members of the ICBM (International Consortium for Brain Mapping) in MNI (Montreal Neurological Institute) space to obtain a spatial average and performing spatial smoothing with an 8 mm full-width-at-half-maximum Gaussian kernel.

Figure 8:
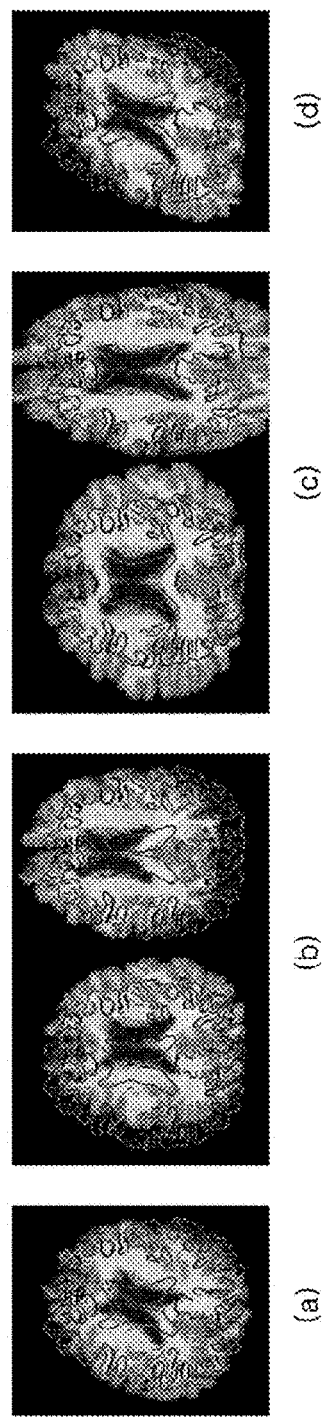
FIG. 8 is a view illustrating four transformations for estimating a transfer matrix.

For example, transformation schemes of four types may be used to estimate the affine transformation matrix. FIG. 8 shows (a) rotation, (b) transformation, (c) scaling and (d) shearing as the four-type transformation schemes. In FIG. 8, the brain shapes before and after transformation are depicted.

The preprocessing unit 22 may estimate the affine transformation matrix for matching the above-described standard T2 image to the GRE image of a diagnostic subject. In this case, although it is described to estimate the affine transformation matrix, various transformation schemes may be used as well as the affine transformation and various kinds of images may be used to estimate the transformation matrix. In this case, although the standard T2 image and the GRE image of a diagnostic subject are used to estimate the transformation matrix, the embodiment is not limited thereto and the standard T1 image and the T1 image of the diagnostic subject may be used. As described above, the standard T2 image (or standard T1 image) converted into a brain shape of a diagnostic subject through the estimated transformation matrix may be generated.

In addition, the preprocessing unit 22 applies the estimated affine transformation matrix to a preset standard brain region map to generate an individual brain region map of a diagnostic subject. In this case, the standard brain map is automated anatomical labeling (AAL) in which the brain region is divided into 116 regions. Although AAL is used in the embodiment, AAL may be replaced as Brodmann's area standard brain region map or Harvard-Oxford standard brain region map.

The feature extracting unit 23 extracts features of 116 brain regions in the individual brain region map of a diagnostic subject generated from the preprocessing unit 22. In this case, the process of extracting the features includes a process of calculating the occupancy ratio of a brain lesion in each of 116 brain regions. In this case, if any brain lesions do not exist in a brain region, the value is calculated as '0' (zero).

The disability type determining unit 24 may determine a disability type based on the brain lesion ratio calculated in the feature extracting unit 23. The disability type may correspond to one of visual impairment, sense impairment, motor impairment, and language impairment. The position of a brain region and reference value of each disability type is previously stored in the storage unit 27 and since the reference value is set as the average of diagnostic subjects who belong to the same disability type, the reference value is not maintained at a fixed value.

As described above, the disability type determining unit 24 may include a classifier configured to determine the reference value of a brain lesion in each of 116 brain regions and may compare the brain lesion ratios of 116 brain regions of the diagnostic subject extracted by the feature extracting unit 23 with the reference values of the brain lesions in the 116 brain regions determined by the classifier such that the disability type determining unit 24 classifies the brain regions, the brain lesion ratios of which exceed the reference values. Thus, the disability type determining unit 24 may determine the disability type of the brain lesion in accordance to the position of the brain region exceeding the reference value and the occupancy ratio of the brain lesion. The position of a brain region of each disability type and the reference value thereof are stored in the storage unit 27. For example, the brain regions (for example, brain regions of A11, A25, A37, A41, A55, A60 and A78) in which the occupancy ratios of brain lesions exceed the corresponding reference values may be detected, such that a set of R11, R25, R37, R41, R55, R60 and R78 representing the occupancy ratios of the brain lesions exceeding the corresponding reference values in the brain regions may be extracted. When the set is processed through the classifier, the disability type corresponding to the set may be obtained. As the classifier repeats the process described above, the accuracy and reliability of the classification may be improved.

The disability degree classifying unit 25 may classify a disability degree of the brain lesion of which the disability type is determined. In more detail, the disability degree classifying unit 25 may generate a classifier configured to classify a disability degree of a diagnostic subject and classify the disability degree of a diagnostic subject through the classifier. The classifier to classify a disability degree determines occupancy ratio and score reference values based on occupancy ratios of brain lesions of the diagnostic subjects having the same disability type and scores obtained through related examinations performed during processes of treating the disabilities of the diagnostic subjects. The brain lesion ratios and scores of the diagnostic subjects may be stored in the storage unit 27 and information stored corresponding to each diagnostic subject may include identification information to distinguish the disability type. For example, a degree of a ratio between a brain region and a brain lesion and a score in a disability type may be matched with each other by using the stored information and estimated to generate a classifier of determining the disability degree.

For example, a related examination performed during a process of treating the disability of a diagnostic subject through an off-line may include an assessment of visual acuity in the case of visual field defect, a movement examination in the case of motor disorder, and a language examination in the case of language disorder. As well as the examinations described above, the related examination may include the examinations required for the purpose of treatment or state check.

The disability degree of a diagnostic subject may be classified through the disability degree classifying unit 25. For example, in the case of a patent of a visual field defect type, the disability type may be classified as hemianopia (blindness in the left or right visual field) or quadrantanopia (blindness in a quarter of the visual field). In the case of a patent of a motor disorder type, the disability type may be classified as limb hemiplegia or leg/arm hemiplegia. In the case of a patent of language disorder, the disability type may be classified as high/low language comprehension ability (based on a language ability evaluation score).

The prognosis predicting unit 26 may predict the prognosis of the disability type determined by the disability type determining unit 24. That is, the prognosis predicting unit 26 may predict the prognosis by analyzing the treatment results of the diagnostic subjects who have the same disability type and the ratios of the brain lesions in a predetermined range with reference to the brain lesion positions, the ratios of brain lesions, the disability types and the treatment results of the diagnostic subjects stored in the storage unit 27. For example, the treatment result may include complete recovery, improvement of %, and incomplete recovery.

The prognosis predicting unit 26 provides the average of the treatment results of the diagnostic subjects who have the same disability type and the ratios of brain lesions of whom are in the preset range, among the treatment results stored in the storage unit 27. Thus, the prognosis prediction may be provided based on the same type of the treatment result stored in the storage unit 27 without relying on the personal experience of a doctor.

Figure 3:
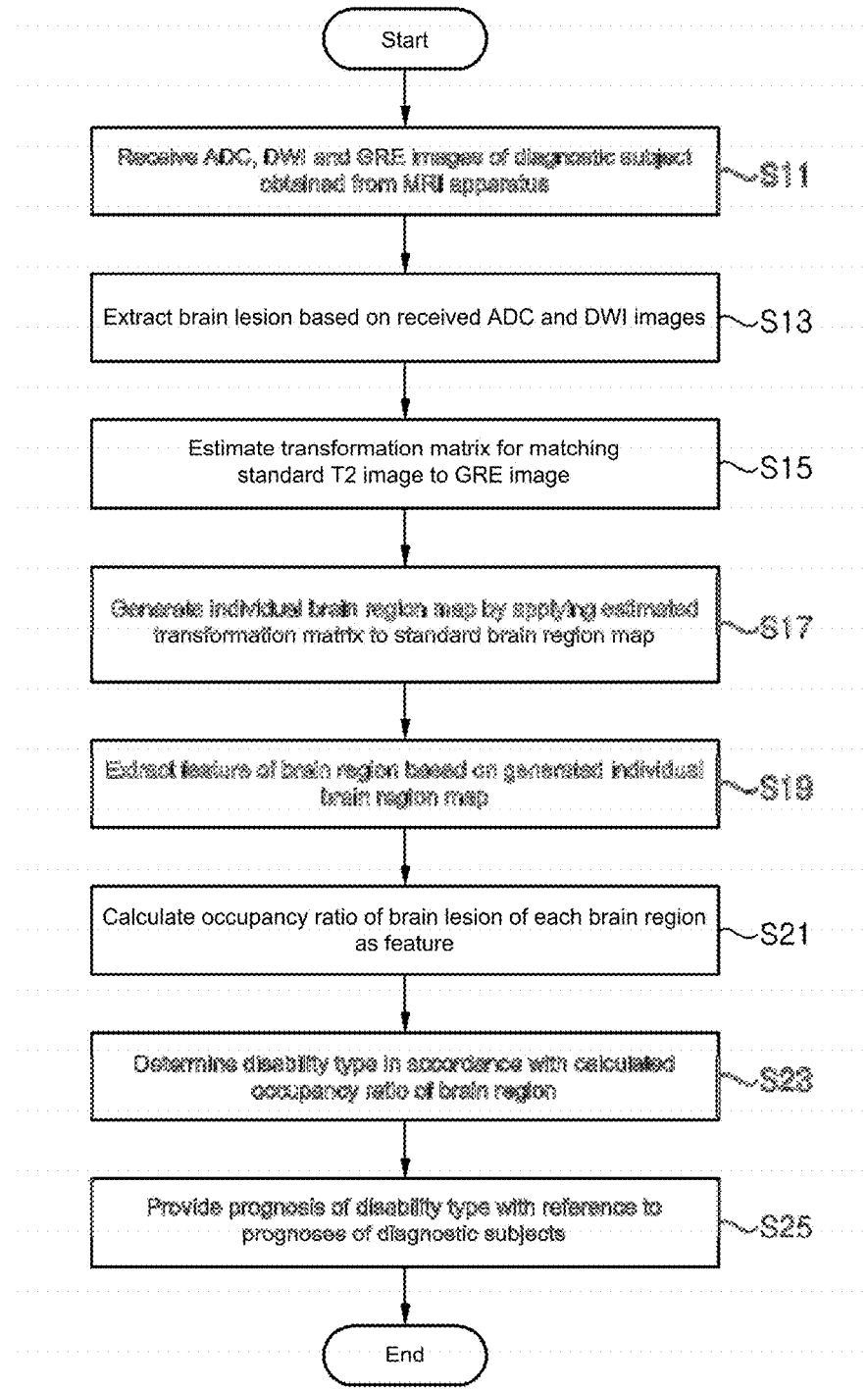
FIG. 3 is a flowchart illustrating a service method of a brain disease diagnosis service apparatus according to an embodiment of the disclosure.

FIG. 3 is a flowchart illustrating a service method of a brain disease diagnosis service apparatus according to an embodiment of the disclosure.

Referring to FIG. 3, in step S11, the rain disease diagnosis service apparatus 20 receives ADC, DWI and GRE images of a diagnostic subject having a brain disease, which are obtained from the MRI apparatus 10.

Figure 4:
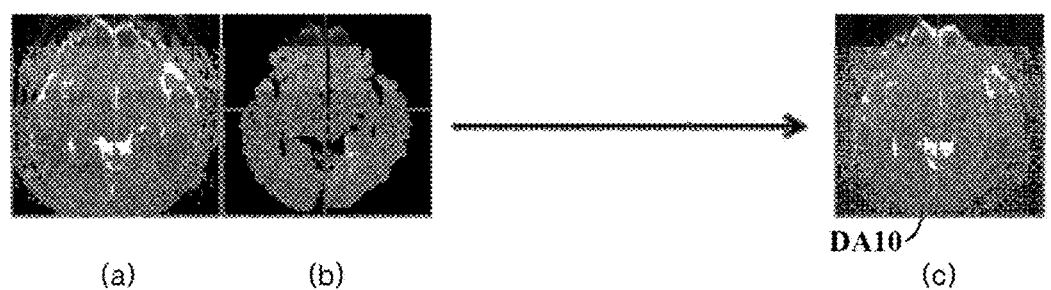
FIG. 4 is a view showing pictures in each of which a brain lesion region, which is extracted based on ADC, DWI, ADC and DWI images obtained from an MRI apparatus, is denoted.

In step S13, the rain disease diagnosis service apparatus 20 extracts a brain lesion based on the received ADC and DWI images. Referring to FIG. 4, (a) of FIG. 4 shows the ADC image, and (b) of FIG. 4 shows the DWI image. The result of matching (a) and (b) of FIG. 4 to each other is shown in (c) of FIG. 4. As shown in (c) of FIG. 4, the brain lesion may be exactly extracted. As shown in (c) of FIG. 4, it is understood that the red region (denoted as 'DA10') is a brain region in which a brain lesion exists.

Then, when any brain lesions are not extracted, the brain disease diagnosis service apparatus 20 does not perform step S15 but finishes the process. When a brain lesion is extracted, the brain disease diagnosis service apparatus 20 performs step S15.

First, in step S15, the brain disease diagnosis service apparatus 20 estimates a transformation matrix for matching the standard T2 image to the GRE image. A standard image for estimating the transformation matrix may be set with reference to the position of the brain lesion extracted in step S13 described above. In the embodiment, it will be described to set the standard T2 image.

Figure 5:
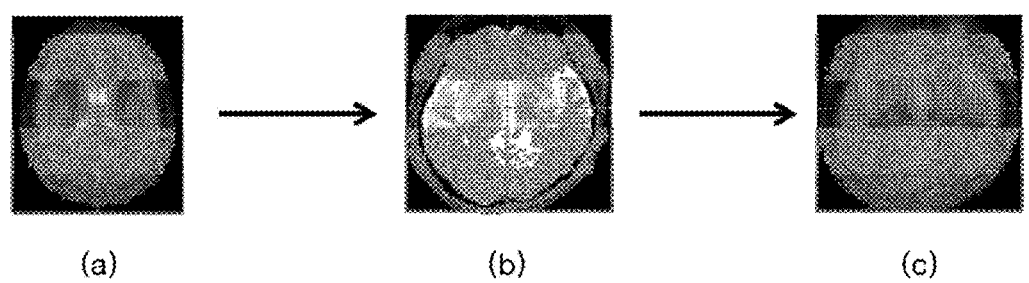
FIG. 5 is a view showing pictures of a standard T2 image, a GRE image obtained from an MRI apparatus, and a transferred standard T2 in which a brain shape of a diagnostic subject is transferred by a transfer matrix estimated to match the standard T2 image with the GRE image.

An affine transformation matrix is estimated to match the standard T2 image shown in (a) of FIG. 5 to the GRE image of the diagnostic subject shown in (b) of FIG. 5. When the affine transformation matrix is estimated, as shown in FIG. 8, four transformation schemes may be used. The standard T2 image transformed into the brain shape of the diagnostic subject with the estimated affine transformation matrix is shown in (c) of FIG. 5.

In step S17, an individual brain region map is generated by applying the transformation matrix estimated in step S15 described above to a standard brain region map. An ML standard brain region map is shown in (a) of FIG. 6 and the individual brain region map generated by applying the transformation matrix to the standard brain region map is shown in (b) of FIG. 6.

In step S19, the brain disease diagnosis service apparatus 20 extracts a feature of a brain region based on the generated individual brain region map of the diagnostic subject. The process of extracting the feature includes a process of extracting the occupancy ratio of a brain lesion of each brain region in the 116-brain region map converted into the brain shape of the diagnostic subject calculated through the feature extracting unit 23.

Figure 6:
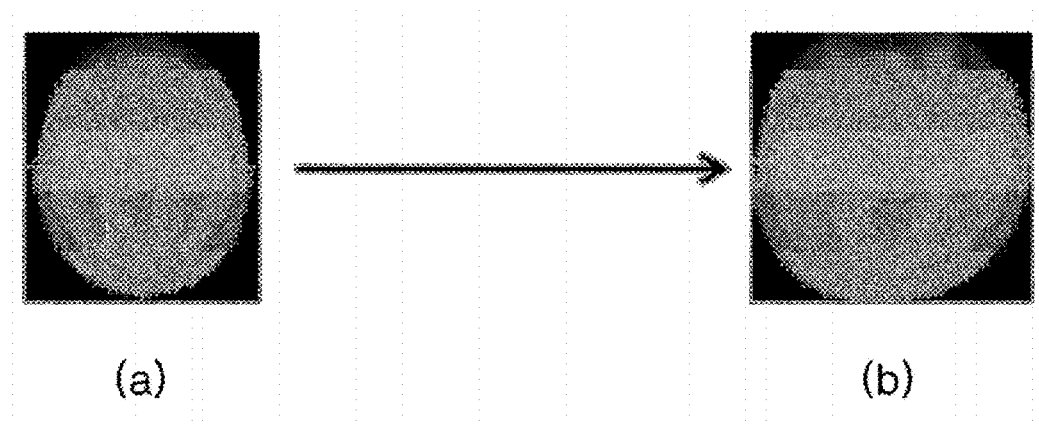
FIG. 6 is a view showing pictures of individual brain region maps of a diagnostic subject, which are created by applying the estimated transformation matrix of FIG. 5 to a standard brain region map.
Figure 7:
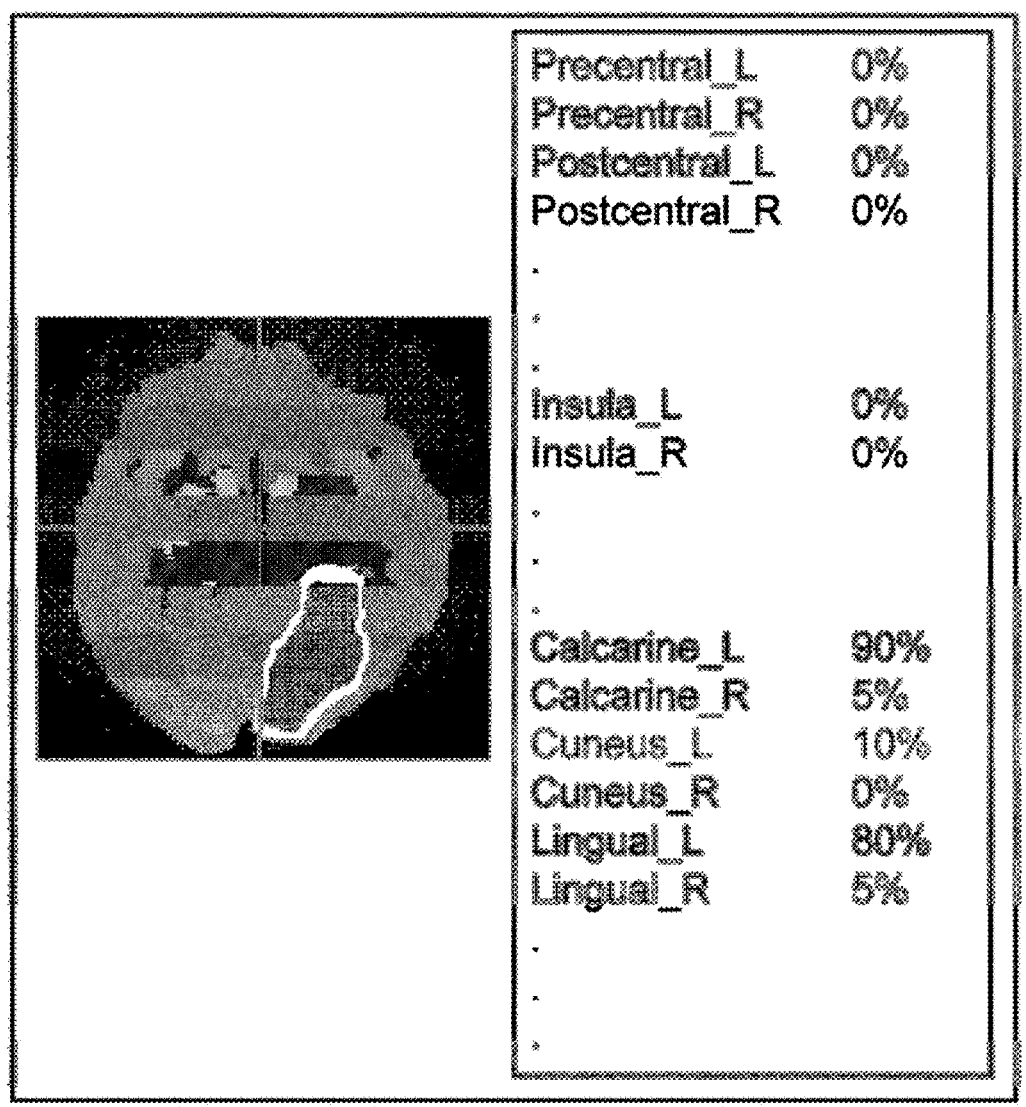
FIG. 7 is a view illustrating occupancy ratios of 116 brain regions into which the standard brain region map of a diagnostic subject depicted in FIG. 6 is divided.

In step S21, the brain disease diagnosis service apparatus 20 calculates the occupancy ratio of a brain lesion of each brain region as the feature. FIG. 7 is a view illustrating occupancy ratios of 116 brain regions into which the standard brain region map of a diagnostic subject depicted in FIG. 6 is divided.

As shown in FIG. 7, in step S23, when a brain lesion exists in a brain region and the occupancy ratio of the brain lesion in the brain region exceeds the preset reference value, the brain disease diagnosis service apparatus 20 determines the disability type defined in the brain region, in which the brain lesion exists, with reference to the occupancy ratio of each brain region. In this case, the brain region in which a brain lesion exists and the reference value thereof may be set in accordance with each disability type and the reference value may be changed by the occupancy ratio of a brain lesion of a diagnostic subject having the same disability type. That is, as described above, as the accumulated data are continuously classified by the classifier, the reference value may be amended.

A process of classifying a disability degree of the diagnostic subject in the determined disability type may be performed after step 23 described above or step S25 described below. The classifier described above may be generated to classify a disability degree and the disability degree of a diagnostic subject may be classified through the classifier.

In step S25, the brain disease diagnosis service apparatus 20 provides a prognosis of the diagnostic subject in the disability type in accordance with a degree of the occupancy ratio of the brain lesion. In this case, the diagnosis is an analysis result obtained with reference to the diagnoses of the diagnostic subjects having the same disability type.

Thus, the result of comprehensively analyzing the treatment results of the diagnostic subjects may be provided to the diagnostic subject having the brain disease as the diagnosis of the disability type without relying on the personal experience of a doctor.

Hereinafter, various embodiments of the present disclosure will be described as follows.

(1) An apparatus for servicing a brain disease diagnosis based on an image obtained from a magnetic resonance imaging (MRI) apparatus, wherein the apparatus includes a receiving unit configured to receive an image of a diagnostic subject obtained from the MRI apparatus, a preprocessing unit configured to estimate a transformation matrix for matching a preset standard image to the image received from the receiving unit and apply the transformation matrix to a preset standard brain region map such that an individual brain region map of the diagnostic subject is generated, a feature extracting unit configured to calculate an occupancy ratio of a brain lesion of each brain region in the individual brain region map of the diagnostic subject generated from the preprocessing unit to extract a feature, and a disability type determining unit configured to determine a disability type based on the occupancy ratio of the brain lesion of each brain region calculated by the feature extracting unit.

(2) An apparatus for servicing a brain disease diagnosis, wherein the image of the diagnostic subject obtained from the MRI apparatus includes apparent diffusion coherent (ADC) diffusion weighted image (DWI) and gradient-echo (GRE) images.

(3) An apparatus for servicing a brain disease diagnosis, wherein the preprocessing unit matches the ADC and DWI images to each other to extract a position of the brain lesion.

(4) An apparatus for servicing a brain disease diagnosis, wherein the standard image includes a standard T2 image, and the preprocessing unit estimates an affine transformation matrix to match the standard T2 image to the GRE image and generates a standard T2 image converted in a brain shape of the diagnostic subject through the affine transformation matrix.

(5) An apparatus for servicing a brain disease diagnosis, wherein the disability type determining unit uses disability types and occupancy ratios of brain lesions of diagnostic subjects to generate a classifier configured to determine a reference value of a brain lesion in each brain region, and determines the disability type based on a position of a brain region of a brain lesion exceeding the reference value determined by the classifier and an occupancy ratio of the brain lesion.

(6) An apparatus for servicing a brain disease diagnosis, wherein the apparatus further includes a disability degree classifying unit configured to classify a disability degree corresponding to the occupancy ratio of the brain lesion of the diagnostic subject based on a reference value set by using occupancy ratios of brain lesions of diagnostic subjects having the same disability type as that determined by the disability type determining unit.

(7) An apparatus for servicing a brain disease diagnosis, wherein the apparatus further includes a prognosis predicting unit predicts a prognosis of the disability type determined by the disability type determining unit in accordance with the occupancy ratio of the brain lesion of each brain region.

(8) An apparatus for servicing a brain disease diagnosis, wherein the prognosis predicting unit provides the prognosis predicted by analyzing treatment results of diagnostic subjects who have a same disability type and occupancy ratios of brain lesions in a predetermined range with reference to brain lesion positions, the occupancy ratios of the brain lesions, disability types and the treatment results of the diagnostic subjects stored in the storage unit.

(9) A method of servicing a brain disease diagnosis based on an image obtained from a magnetic resonance imaging (MRI) apparatus, wherein the method includes receiving an image of a diagnostic subject obtained from the MRI apparatus, estimating a transformation matrix for matching a preset standard image to the received image and applying the transformation matrix to a preset standard brain region map such that an individual brain region map of the diagnostic subject is generated, calculating an occupancy ratio of a brain lesion of each brain region in the generated individual brain region map of the diagnostic subject to extract a feature by, and determining a disability type based on the occupancy ratio of the brain lesion of each brain region calculated.

(10) A method of servicing a brain disease diagnosis, wherein the image of the diagnostic subject obtained from the MRI apparatus includes apparent diffusion coherent (ADC) diffusion weighted image (DWI) and gradient-echo (GRE) images, and the generating of the individual brain region map comprises matching the ADC and DWI images to each other to extract a position of the brain lesion.

(11) A method of servicing a brain disease diagnosis, wherein the standard image includes a standard T2 image, and the generating of the individual brain region map includes estimating an affine transformation matrix to match the standard T2 image to the GRE image, and generating a standard T2 image converted into a brain shape of the diagnostic subject through the affine transformation matrix.

(12) A method of servicing a brain disease diagnosis, wherein, in the determining of the disability type, disability types and occupancy ratios of brain lesions of diagnostic subjects are used to generate a classifier configured to determine a reference value of a brain lesion in each brain region, and the disability type is determined based on a position of a brain region of a brain lesion exceeding the reference value determined by the classifier and an occupancy ratio of a brain lesion.

(13) A method of servicing a brain disease diagnosis, wherein the method further includes classifying a disability degree corresponding to the occupancy ratio of the brain lesion of the diagnostic subject based on a reference value set by using occupancy ratios of brain lesions of diagnostic subjects having the same disability type as that determined.

(14) A method of servicing a brain disease diagnosis, wherein the method further includes predicting a prognosis of the disability type determined by the disability type determining unit in accordance with the occupancy ratio of the brain lesion of each brain region.

(15) A method of servicing a brain disease diagnosis, wherein the method further includes, before predicting the a prognosis, classifying a disability degree corresponding to the occupancy ratio of the brain lesion of the diagnostic subject based on the disability type and a reference value set by using occupancy ratios of brain lesions of diagnostic subjects having a same disability type.

According to the brain disease diagnosis service apparatus and brain disease diagnosis service method of the disclosure, when the brain lesion is extracted by using the images obtained from the MRI apparatus, the disability type may be determined based on the result of calculating the occupancy ratio of the brain lesion of each brain region in the individual brain region map of the diagnostic subject generated by applying the transformation matrix estimated with the images of the diagnostic subject and the standard image to the standard brain region map, so that the brain disease is quantitatively and generally determined as well as the disability type.

In addition, according to the brain disease diagnosis service apparatus and brain disease diagnosis service method of the disclosure, the prognosis may be quantitatively and generally provided in accordance with the occupancy ratio of the brain lesion of each brain region of the diagnostic subject by analyzing the treatment results of the diagnostic subjects having the same disability type.

In addition, according to the brain disease diagnosis service apparatus and brain disease diagnosis service method of the disclosure, the normalization for generating the individual brain region map of the diagnostic subject is performed by estimating the transformation matrix for matching the predetermined standard T2 image to the GRE image of the diagnostic subject and applying the estimated transformation matrix to the standard brain region map, so that the feature of the brain lesion may be easily extracted.

The invention claimed is:

1. An apparatus for servicing a brain disease diagnosis based on an image obtained from a magnetic resonance imaging (MRI) apparatus, the apparatus comprising a processor, wherein said processor comprises:
   a receiving unit configured to receive an image of a diagnostic subject obtained from the MRI apparatus;
   a preprocessing unit configured to
      estimate a transformation matrix for matching a preset standard image to the image received from the receiving unit and
      apply the estimated transformation matrix to a preset standard brain region map such that an individual brain region map of the diagnostic subject is generated;
   a feature extracting unit configured to calculate an occupancy ratio of a brain lesion of each brain region in the generated individual brain region map of the diagnostic subject
   a disability type determining unit configured to determine a disability type based on the calculated occupancy ratio of the brain lesion of each brain region;
   a disability degree classifying unit configured to classify a disability degree corresponding to the calculated occupancy ratio of the brain lesion of the diagnostic subject, based on a reference value set by using occupancy ratios of brain lesions of diagnostic subjects having the same disability type as that determined by the disability type determining unit and
   a prognosis predicting unit configured to predict a prognosis of the determined disability type in accordance with the classified disability degree.

2. The apparatus of claim 1, wherein the image of the diagnostic subject obtained from the Mill apparatus comprises apparent diffusion coherent (ADC), diffusion weighted image (DWI) and gradient-echo (GRE) images.

3. The apparatus of claim 2, wherein the preprocessing unit is configured to match the ADC and DWI images to each other to extract a position of the brain lesion.

4. The apparatus of claim 2, wherein
   the standard image comprises a standard T2 image, and
   the preprocessing unit is configured to
      estimate an affine transformation matrix to match the standard T2 image to the GRE image and
      generate standard T2 image converted in a brain shape of the diagnostic subject through the estimated affine transformation matrix.

5. The apparatus of claim 1, wherein the disability type determining unit is configured to
   generate a classifier, by using disability types and occupancy ratios of brain lesions of diagnostic subjects, to determine a reference value of a brain lesion in each brain region, and
   determine the disability type based on a position of a brain region exceeding the reference value determined by the classifier and the calculated occupancy ratio of the brain lesion.

6. The apparatus of claim 1, further comprising
   a storage unit,
   wherein the prognosis predicting unit is configured to provide the prognosis predicted by analyzing treatment results of diagnostic subjects who have the same disability type and occupancy ratios of brain lesions in a predetermined range with reference to brain lesion positions, the occupancy ratios of the brain lesions, disability types and the treatment results of the diagnostic subjects stored in the storage unit.

7. A method of servicing a brain disease diagnosis based on an image obtained from a magnetic resonance imaging (MRI) apparatus, the method comprising:
   receiving an image of a diagnostic subject obtained from the MRI apparatus;
   estimating a transformation matrix for matching a preset standard image to the received image and applying the estimated transformation matrix to a preset standard brain region map such that an individual brain region map of the diagnostic subject is generated;
   calculating an occupancy ratio of a brain lesion of each brain region in the generated individual brain region map of the diagnostic subject to extract a feature by; and determining a disability type based on the occupancy ratio of the brain lesion of each brain region;

classifying a disability degree corresponding to the calculated occupancy ratio of the brain lesion of the diagnostic subject based on a reference value set by using occupancy ratios of brain lesions of diagnostic subjects having the same disability type as that determined; and predicting a prognosis of the determined disability type in accordance with the classified disability degree.

8. The method of claim 7, wherein the image of the diagnostic subject obtained from the MRI apparatus comprises apparent diffusion coherent (ADC), diffusion weighted image (DWI) and gradient-echo (GRE) images, and the generating of the individual brain region map comprises matching the ADC and DWI images to each other to extract a position of the brain lesion.

9. The method of claim 8, wherein the standard image comprises a standard T2 image, and the generating of the individual brain region map comprises estimating an affine transformation matrix to match the standard T2 image to the GRE image, and generating a standard T2 image converted into a brain shape of the diagnostic subject through the estimated affine transformation matrix.

10. The method of claim 7, wherein the determining of the disability type comprises generating a classifier, by using disability types and occupancy ratios of brain lesions of diagnostic subjects, to determine a reference value of a brain lesion in each brain region, and determining the disability type based on a position of a brain region of a brain lesion exceeding the reference value determined by the classifier and the calculated occupancy ratio of a brain lesion.

\* \* \* \* \*